US006616067B1

(12) United States Patent
Hunter

(10) Patent No.: US 6,616,067 B1
(45) Date of Patent: Sep. 9, 2003

(54) DISPENSING APPARATUS

(75) Inventor: William E. Hunter, 4691 1st Ave. NW., Naples, FL (US) 34119

(73) Assignee: William E. Hunter, San Jose, CA (US)

( * ) Notice: Subject to any disclaimer, the term of this patent is extended or adjusted under 35 U.S.C. 154(b) by 0 days.

(21) Appl. No.: 10/120,049

(22) Filed: Apr. 11, 2002

(51) Int. Cl.[7] .......................... A61M 11/06; B05B 7/32

(52) U.S. Cl. ....................... 239/338; 239/337; 239/346; 239/355; 239/367; 239/373; 239/375; 222/209

(58) Field of Search ................................ 239/337, 338, 239/346, 355, 363, 367, 373, 375, 361, 362; 222/209, 400.8

(56) References Cited

U.S. PATENT DOCUMENTS

| | | | | | |
|---|---|---|---|---|---|
| 1,646,081 | A | * | 10/1927 | Conklin | 239/373 |
| 1,679,104 | A | * | 7/1928 | Trautman | 222/209 |
| 1,825,608 | A | * | 9/1931 | Shaukis | 239/353 |
| 1,953,102 | A | * | 4/1934 | Brown | 239/373 |
| 2,066,977 | A | * | 1/1937 | Iler | 222/209 |
| 2,326,641 | A | * | 8/1943 | Heeter et al. | 222/209 |
| 2,342,940 | A | * | 2/1944 | Janke | 222/209 |

* cited by examiner

*Primary Examiner*—Robin O. Evans

(57) ABSTRACT

The invention is directed to a dispenser attachment to be mounted on a standard bottle having exterior threads at its neck. The attachment has two side arms emanating from a center. One arms has at its outer end a pressuring air bulb attached thereto. The outer end of the bulb has a one-way ball valve attached therein and another one-way ball valve is attached within the other end of the bulb. The pressurized air generated by the bulb enters directly into the interior of the bottle by way of a passage way. The passage way has a bypass just downstream of said one-way ball valve to accommodate the inward movement of the ball. The pressurized fluid in the bottle is controlled by a single unit ball valve assembly having a push button under a bias of a spring. The push button is located at the top of the attachment and is flush with its surface.

3 Claims, 2 Drawing Sheets

DISPENSING APPARATUS

CROSS REFERENCE TO RELATED APPLICATIONS (none)

STATEMENT REGARDING FED SPONSORED R & D (none)

BACKGROUND OF THE INVENTION

The invention pertains to a dispensing apparatus, particularly, it is directed to a dispensing apparatus adapted to be used in combination with a 2 liter soda bottle. It is a well known fact that 2 liter bottles of, for example, containing soft drinks that are under the influence of a carbonation, the carbonation quickly dissipates once the bottle is opened. The fact that the bottle has a volume of at least 2 liters, makes it more difficult to maintain the carbonation, or the fizz, because the content of the soft drink cannot be drunk all at the same time. It is desirable to maintain the benefit of the carbonation over a longer span of time. many attempts have been made to maintain the carbonation in the container. Many other attempts have been made to construct a dispenser apparatus that is useful with containers having just a plain liquid therein which is to be dispensed.

U.S. Pat. No. 1,679,104 illustrates a beverage bottle having a pressure relieve valve that allows the internal pressure of the fluid to escape to the environment. The attachment has to be applied to a bottle by way of a squeeze and expansion device.

U.S. Pat. No. 1,968,316 shows a liquid dispenser wherein the fluid in a container is pressurized by a squeeze bulb including a pressurization attachment that is sealed to the top of a container by squeezing a seal on top of a neck of a bottle.

U.S. Pat. No. 2,028,553 shows a dispensing apparatus on a container that has an operating pump on of the attachment that operates as the dispenser.

U.S. Pat. No. 2,431,596 is a cream dispensing device that needs no further discussion, although some of the elements are similar to applicant's disclosure.

U.S. Pat. No. 3,198,405 is a beer bottle dispenser that has a pump that may be used to buildup air pressure within a container to a desired amount, whereupon the normally dispensing valve may be opened to allow the air pressure in the can to force the liquid through a conduit for discharge into a spout.

U.S. Pat. No. 4,119,244 discloses a hand-operated piston pump which is mountable on a neck of a bottle having a first portion outwardly embracing the neck and a second portion inwardly extending into the neck of the bottle.

U.S. Pat. No. 4,383,622 is directed to a sanitary wash bottle kit assembly wherein a resilient pump bulb is disposed adjacent a neck of a container.

U.S. Pat. No. 4,877,158 shows a fluid dispensing apparatus that includes a body portion supporting a pump assembly and a valve assembly. The body portion has a ring assembly that allows the body portion to rotate around a top of the container.

U.S. Pat. No. 4,984,717 discloses a pressurized, refillable, reusable container which is comprised of a top, a base and at least one wall attached between the top and the base which together define an enclosed space. A valve is provided through the top of the container which valve has a single releasable passageway for filling, pressurizing and emptying the container. This is not the inventive concept of applicant's disclosure.

U.S. Pat. No. 5,040,703 shows a pressurization system and a dispensing system that includes a pressure-generating gas supply unit including a battery operated air compressor.

U.S. Pat. No. 5,738,254 shows the use of a pressurizing dispenser for removable attachment to the threaded neck of a carbonated beverage container which includes having an integrally formed handle and a hollow collar with a threaded seal ring therein for threaded engagement with the neck of the container and including a central opening in alignment with the discharge opening of the container.

U.S. Pat. No. 5,823,372 describes a pump which is adapted for insertion between a cap and a carbonated-beverage bottle for re-pressurizing the interior of the bottle with air. A pump is adapted for engaging an inside recess of a standard bottle cap.

U.S. Pat. No. 5,836,364 shows a refillable bottle that is constructed to be capable of holding fluids above atmospheric pressure and has a threaded cap. The top of the threaded cap has at least one valve having a single resalable passageway for filling.

U.S. Pat. No. 6,279,787 discloses a beverage container. A pumping lid assembly for selectively opening and closing is inserted the container body is inserted into the opening of the container body. A plunger assembly is fitted into the central portion of the pump housing and is designed pressurize air into the interior of the container while being moved downwardly to suck air from the outside while being moved downwardly.

BRIEF SUMMARY OF THE INVENTION

The inventive concept includes a bottle cap that contains; a simple air pump for the purpose of repressuring the interior of an industry standard 1.5, 2.0 or 3.0 Liter soda bottle with ambient air, a one-way check valve is included which will prevent the pressurized air contained within the bottle from escaping from the interior. Included in the replacement bottle cap is a pick-up tube used to channel the liquid from the bottom of the bottle. Further included is a flow control valve when opened allows the pressurized air within the container to force the liquid contents from the bottom of the container or bottle to the flow to the control valve. Included also is a spout that channels the liquid content from the flow control valve to the exterior of the cap housing and on a location on the cap for advertising purposes.

DETAILED DESCRIPTION OF THE INVENTION

Figure 1:
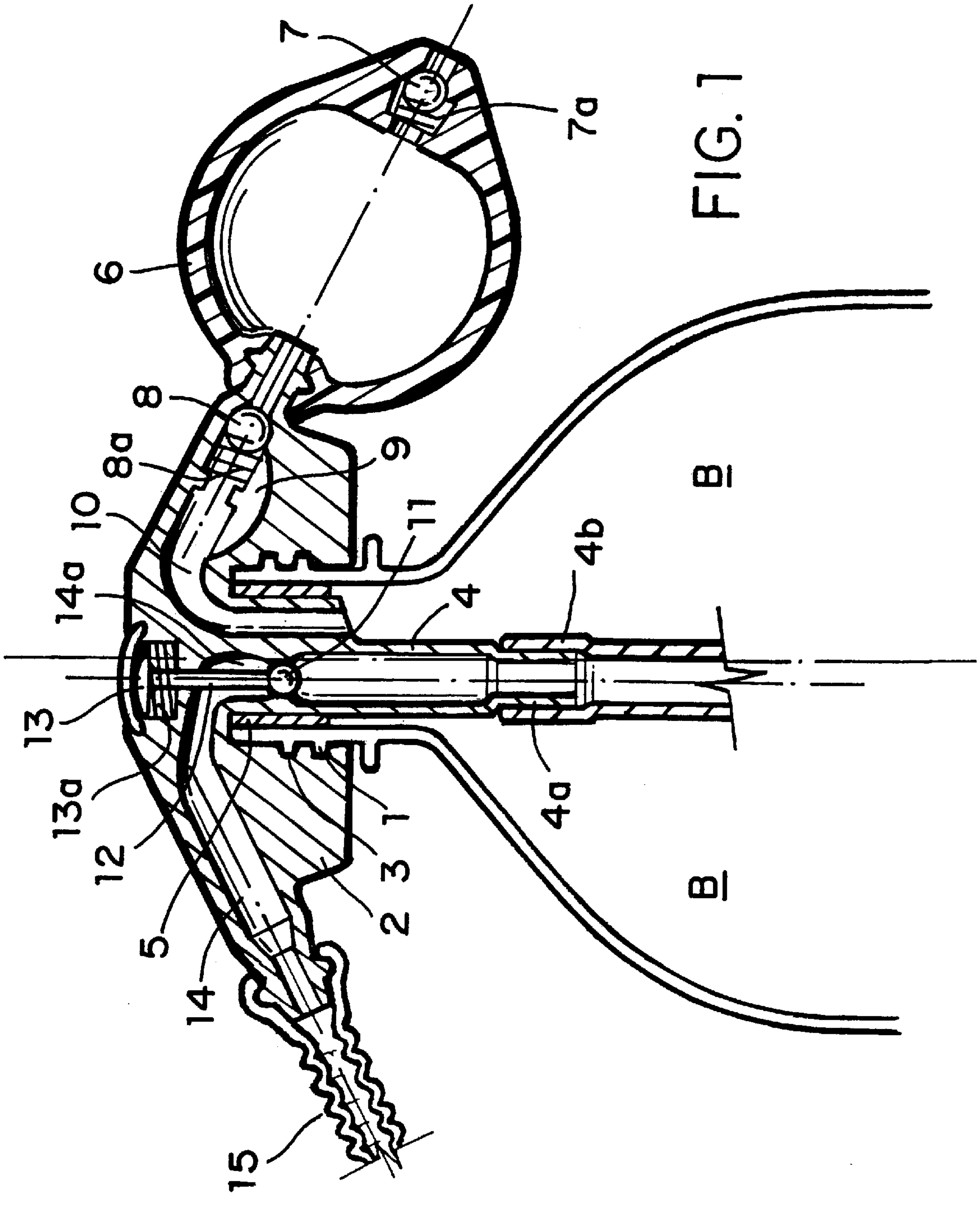
FIG. 1 shows a cross section of the bottle cap exposing its interior.

Turning now to FIG. 1, the inventive cap of the fluid dispensing attachment is designated as 2 while the bottle to which the attachment is to be attached is designated as B. The attachment 2 is attached to the exterior threads 1 of the bottle B while being screwed into the interior threads 3. The attachment 2 at its center and at its bottom has a fluid expelling tube 4 which will expel the fluid out of the bottle B when it is under pressure. The fluid expelling tube 4 is subdivided into two sections. A first section 4 is integrally molded with the attachment B and has a lower section 4*a* which is reduced in its diameter. The reduced diameter corresponds to the inner diameter of the tube 4*b* which can be slipped over the reduced section 4*b* to thereby form a tight fluid connection into the bottom of the bottle. The attachment 2 is sealed against the interior neck of the bottle by way of a seal 5 which is placed within the interior neck of the bottle B.

The attachment 2 is being constructed of a two-arm device, wherein one arm has a compressible bulb 6 attached to the outer end of the arm. At the outer end of the bulb 6 there is located a one-way check valve 7 in the form of a ball which is under a spring pressure 7*a* to close the ball valve under normal conditions. When the bulb is being squeezed, the ambient air is expelled into the interior of the bottle B. When the pressure on the bulb 6 is released, the check valve 7 allows more ambient air to enter into the bulb 6. The other end of the bulb 6 also has a one-way check valve 8 which operates in the opposite manner as does the check valve 7. In this manner, when the bulb 6 is being squeezed, the ambient air will freely move into the bottle B by way of the passage 9 and 10 to pressurize the content within the bottle. When not under pressure of the bulb 6, the ball 8 will reseal itself under the bias of the spring 8*a*. Once the interior fluid in the bottle B is pressurized, the fluid cannot escape through the spout 14 because of the sealing ball 11 which seals against the passage 14. The ball 11 is connected to a stem 12 which in turn is connected to a push button 13 which is biased upwardly by the spring 13*a* to thereby form a single unit. It is noted that the push button 13 is located at the very top of the attachment and is flush therewith. The reason for this is that the standard bottle of soda has a certain height and by the time the attachment 2 is added to its top, the new height created thereby, may not fit between any two shelves within a refrigerator. With reference to FIG. 1, it should also be noted that the outlet passage 14 close to the ball valve is somewhat enlarged at 14*a* to allow the fluid which is under pressure to easily escape from its seal into the passage 14 and from there into the spout 15.

Figure 2:
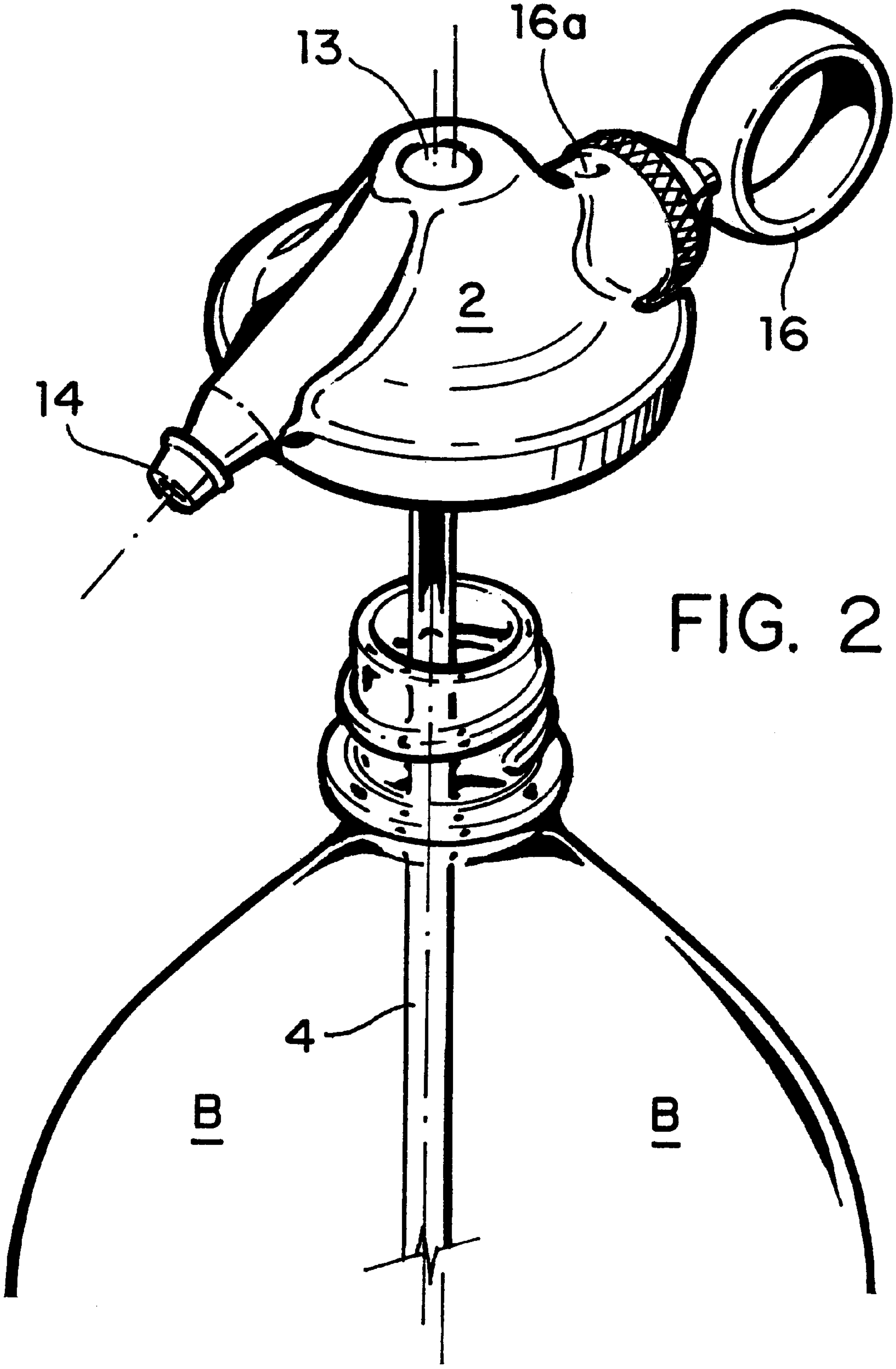
FIG. 2 shows an exploded and a perspective view of the bottle cap of FIG. 1.

Turning now to FIG. 2 which is an exploded and perspective view of the dispensing system of the inventive concept. In this FIG. like reference characters have been used to identify the same elements that were disclosed in FIG. 1. In this FIG. 2, the bulb type compressor 6 (FIG. 10) has been replaced with a standard push button pump 16 which is operated by a plunger 16 which is well known in the art. The intake valve 16*a* operates in the same manner as the intake air valve 7 in FIG. 1.

I claim:

1. A dispenser attachment top adapted to be installed on exterior threads of a standard bottle, said dispenser top is constructed of two arms emanating from a center, a first of said two arms having a pressurization sqeezable bulb attached at an end thereof, said bulb having a one-way ball valve attached therein at a first end thereof and having another one-way ball valve attached therein at another end thereof, a single unit ball valve assembly being installed at said center operable to block any flow of fluid from an interior of said bottle and operable to expel fluid from an interior of said bottle when operated by a push button assembly located at a top of said dispenser and is under a bias of a spring, said push button is flush and even with a top surface of said dispenser attachment, an aspiration tube being connected to a bottom of said center unit valve assembly, a dispensing spout located at a second end of said two arms.

2. The dispenser attachment top of claim 1, wherein said aspiration tube consists of two parts, a first part being an integral part of said dispenser attachment top and a second part being removably attached to said first part.

3. The dispenser attachment top of claim 1, wherein said fluid expelling tube has a constriction therein, said constriction forming a seat against which said ball of said one piece valve assembly will seat and block the fluid from being expelled.

* * * * *